United States Patent [19]

Baumgart

[11] Patent Number: 5,474,553
[45] Date of Patent: Dec. 12, 1995

[54] SYSTEM FOR SETTING TUBULAR BONE FRACTURES

[75] Inventor: Rainer Baumgart, Athener Platz 11, 8000 Munich 90, Germany

[73] Assignees: Rainer Baumgart, Munich; Augustin Betz, Starnberg; Reiner Seibold, Haag, all of Germany

[21] Appl. No.: 367,922

[22] Filed: Jan. 3, 1995

Related U.S. Application Data

[63] Continuation of Ser. No. 623,948, Apr. 18, 1990, filed as PCT/EP90/00622, abandoned.

[30] Foreign Application Priority Data

Apr. 18, 1989 [DE] Germany ............... 39 12 703.6

[51] Int. Cl.⁶ ............................................ A61B 17/80
[52] U.S. Cl. ............................ 606/71; 606/70; 606/73
[58] Field of Search ...................... 606/61, 62, 70, 606/71, 69, 105, 59, 57, 58, 72, 73, 96

[56] References Cited

U.S. PATENT DOCUMENTS

| | | | |
|---|---|---|---|
| 4,219,015 | 8/1980 | Steinemann | 606/69 |
| 4,338,926 | 7/1982 | Kummer et al. | 606/62 |
| 4,408,601 | 10/1983 | Wenk | 606/69 |
| 4,429,690 | 2/1984 | Angelino-Pievani | 606/69 |
| 4,456,004 | 6/1984 | Kenny | 606/57 |
| 4,683,878 | 8/1987 | Carter | 606/97 |
| 4,794,918 | 1/1989 | Wolter | 606/69 |
| 5,013,315 | 5/1991 | Barrows | 606/71 |
| 5,057,111 | 10/1991 | Park | 606/69 |

FOREIGN PATENT DOCUMENTS

| | | | |
|---|---|---|---|
| 13862 | 8/1980 | European Pat. Off. | 606/69 |
| 0177270 | 4/1986 | European Pat. Off. | |
| 0240034 | 7/1987 | European Pat. Off. | |
| 742618 | 3/1933 | France . | |
| 675531 | 10/1990 | Switzerland | 606/69 |
| 2075346 | 11/1981 | United Kingdom . | |

OTHER PUBLICATIONS

De Puy brochure "Molybdenum Steel Bone Plates and Screws" 1943, author unknown.
Park, Joon Bu, *Biomaterials Science and Engineering*, Plenum Press, New York, 1984, pp. 11–17.

*Primary Examiner*—Stephen C. Pellegrino
*Assistant Examiner*—Guy V. Tucker
*Attorney, Agent, or Firm*—John F. A. Earley; John F. A. Earley, III

[57] ABSTRACT

The setting device for tubular bone fractures (3,4) consists of a longitudinally extended flattened setting element (20) and of bone screws (10), which in each case are connected to one other by means of a screw (11) and a cone (16) in addition to a taper segment section (15). The setting element (20) has an essentially rectangular cross-section of tissue-compatible high-density material, in particular of implant steel. In each of the two end sections (21) of the setting element (20), at least two bores are provided, which extend through the opposite wide sides thereof. The bone screws (10) are guided through these bores. The setting element (20) consists integrally of the two relatively rigid end pieces (21) and a connection piece (31) lying therebetween. This connection piece (31) is in comparison with the end sections (21) elastic as its cross-section is smaller than that of the end sections (21). The compact setting device formed in this way can be implanted under the skin and enables transverse forces as well as moments of flexion and torsion in the area of the fracture to be eliminated, without the implantation causing additional circulatory disturbances. Further, the normal force in the fracture area can be adjusted.

12 Claims, 3 Drawing Sheets

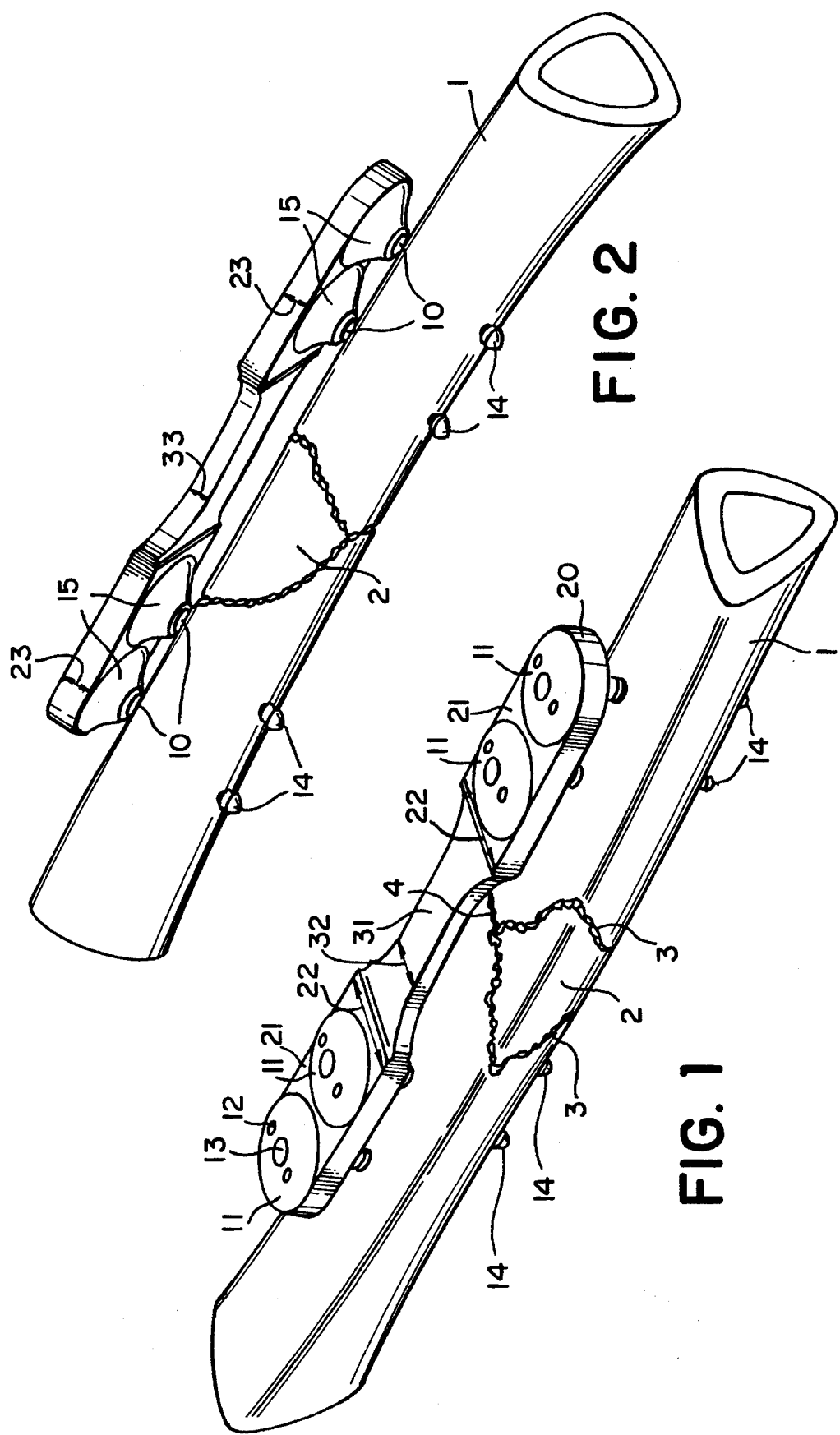

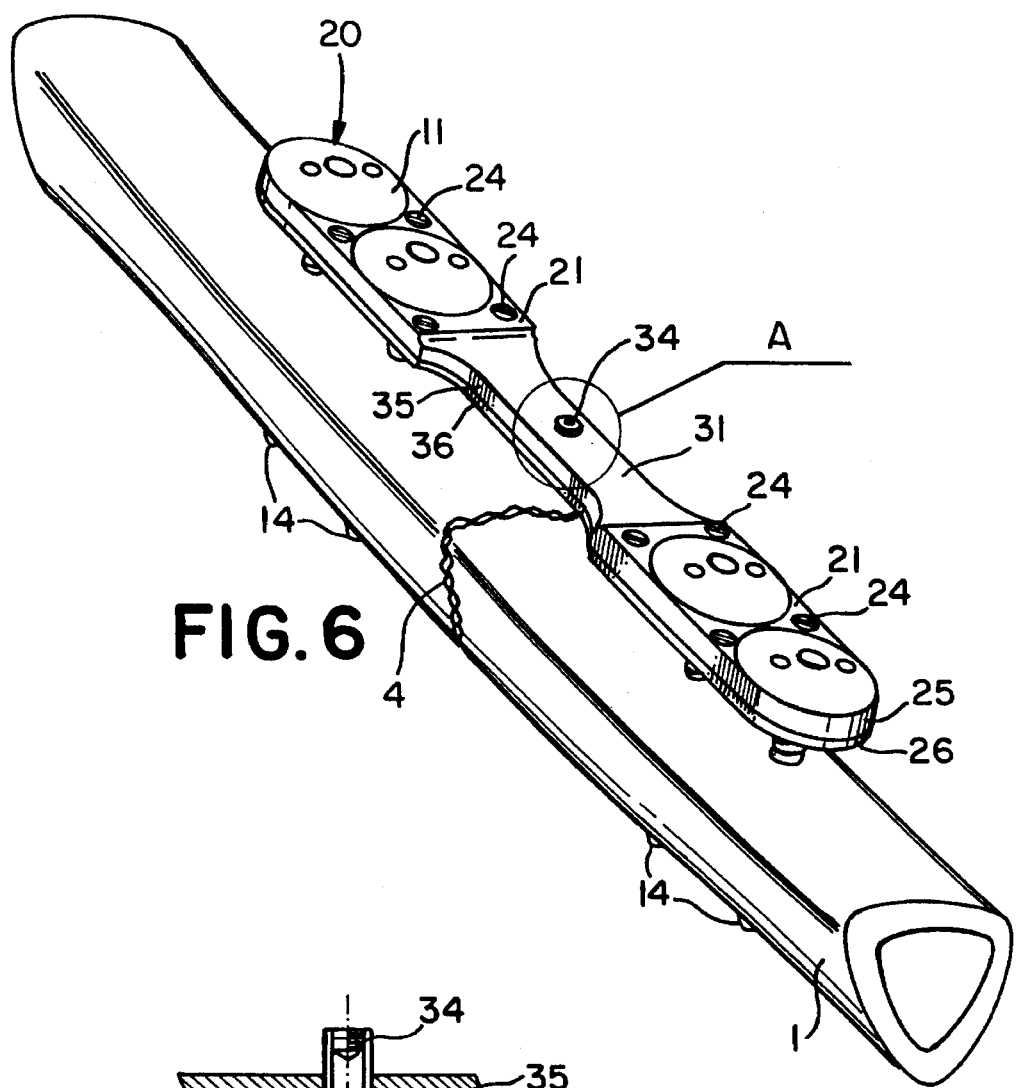
FIG. 6
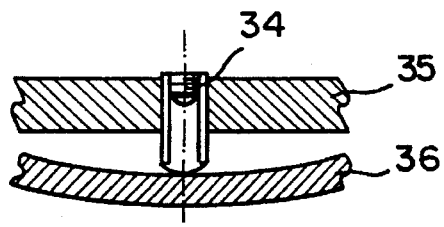
FIG. 7
FIG. 8

SYSTEM FOR SETTING TUBULAR BONE FRACTURES

This is a continuation of application(s) serial number 07/623,948 filed on Apr. 18, 1990, filed as PCT/EP90/00622, now abandoned.

BACKGROUND OF THE INVENTION

1. Field of the Invention

The invention concerns a setting device for the fractures of tubular bones, consisting of a longitudinally extended flattened setting element, with an essentially rectangular cross-section, of tissue compatible high-density material, in particular implant steel, in each end section of which there are at least two bores which extend through the opposite wide sides, and bone screws which are guided through these bores.

2. Description of the Related Art

The setting device is most commonly used on fractures of the long tubular bones of the lower extremities.

Operative stabilization of tubular bone fractures has hitherto been carried out by using plate osteosynthesis, marrow pinning (intramedullary nailing) or an external setting device. The choice of the stablilsation procedure is dependent, on the one hand, on the specific type of fracture and, on the other, is decisively determined by the significance that the surgeon attributes to the biomechanical and the biological procedures during the healing of the bone fracture.

The healing of the bone fracture is assisted if there is no relative movement between the two fractured pieces of bone. It is the aim of every conservative and operative measure to minimise these relative movements.

However, recent investigations suggest that this complete immobilisation is not necessary to the same extent in all phases of fracture healing for all directions of movement and, on the contrary, micromovements in the axial direction of the healing of the fractured bone could even be beneficial. Stabilising systems such as the marrow pin and the external setting device do, under certain conditions, permit an axial compression of the fractured bone ends and the forming callus respectively, dependant on the body weight. This method of assisting fracture healing can always be applied following an initial phase if either an uncomplicated type of fracture or the method of setting used means that no shearing stresses or torsion pressures are to be expected in the fracture gap.

The biological aspects of the healing of fractured bones predominantly concern the blood vessel supply to the newly forming bone. In this case, the periosteum which surrounds the outside of all healthy bone, plays a decisive role, but so, too, does the marrow cavity.

It is therefore possible to compile the following requirements for a setting system in the tubular bone area, namely an exclusion of all transverse forces, as well as of flexural and torsional moments, from the area of the fracture, a normal force, which is applied as required, in the area of the fracture, and no additional circulatory disturbances caused by the method of setting in the area of the fracture. The initially mentioned methods of setting only partially fulfil these requirements.

Plate osteosynthesis, whereby a dish-shaped multi-holed plate lies adjacent to the periosteum over a relatively great length, but, most importantly, the area of the fracture, can, because of circulatory disturbances, lead to delays in the healing and to bone necroses.

Marrow pinning or lock nailing, whereby a metal pin which fills the marrow cavity is pushed into the inside of the tubular bone, can likewise lead to considerable circulatory disturbances, though in this case they come from the inside of the tubular bone. A central splintage near the neutral fibre is, in addition, not a good method of protection against alternating flexural stresses in the area of the fracture.

The external setting device is concerned with a stabilising system whereby screws are anchored-proximally and distally related to the fracture area-into the bone and pass to the outside through the skin, where they are connected to a stable force support device. A setting system of this type is not in immediate proximity to the fracture aperture and does not, therefore, lead to circulatory disturbances. There is, however, an important disadvantage in that the transmission of force to the force support device occurs via the bone screws, which are long and therefore elastic in all directions, thus rendering it difficult to estimate the force gradient across the setting device and the bone respectively. A dynamic adjustment according to requirements, i.e. permitting normal forces in a later stage of the healing process of the bone fracture is usually only possible in a limited manner as, due to the large distance between the bone axis and the force support device and to flexural moments in the force support device which is connected therewith, a tilting or jamming of the system usually occurs. In addition an external stabilizing system signifies a considerable danger of infection and requires intensive nursing.

A known stabilization system for fractures in the vertebral area renders possible, by means of its compact construction, implantation under the skin, so that the risk of infections is reduced and patient comfort is improved. However, due to its construction, this rigid system is not suited to the stabilization of tubular bone fractures and with regard to the dynamic alteration possibilities it only offers a gradual improvement in comparison with the external setting system.

SUMMARY OF THE INVENTION

The object on which the invention is based is to form the setting device initially mentioned in such a way that it can be implanted under the skin, eliminates transverse forces as well as flexural and torsional moments in the area of the fracture, enables metering of the normal force in the area of the fracture and reduces circulatory disturbances in the fracture area to a minimum.

Starting from the setting device of the initially mentioned type, the object is achieved in that the setting element is equipped with a connection section, between the rigid end sections which are provided with anchorage devices for the bone screws, the cross section of which connection section is smaller than that of the end sections.

The setting device according to the invention has a flattened force support device of implant steel, which is positioned in the vicinity of the fractured tubular bone, avoiding any surface contact with the tubular bone. Between the two rigid end sections of this force support carrier or setting element there is a central connection piece, which, in comparison with the end sections, shows a certain elasticity. The end sections accommodate at least two bone screws each, which are firmly held in the stable outer layer of the tubular bone at a sufficient distance from the fracture zone. The entire stabilizing system is built in an extremely compact manner and makes implantation under the skin possible.

The setting device can be realised as a modular system. Thereby the bone screws, as well as the fastening of the bone screws in the force support device, are standardized. The setting element itself forming the force support device is integral or made of a single piece, and is also provided with standardized end sections, while the central connecting section can be manufactured in various strengths, so that the surgeon can select the optimum force support device depending on the weight of the patient and the type of fracture.

In the case of setting devices according to the invention, the cross-sectional area which is bordered by two narrow sides and two wide sides of the connecting section of the setting device is reduced by reducing the dimensions of the narrow sides, or the dimensions of the wide sides, or the dimensions of the narrow and wide sides, in relation to the end sections. In this connection, the reduction of the dimensions of the narrow sides of the connecting section like the reduction of the dimensions of the wide sides of the connecting section is conveniently 30 to 70%.

The reduction of the cross-section in the direction of the narrow side of the connection section leads to normal forces occuring in the fracture area depending upon the load on the bone. The side of the bone which faces away from the setting element is in this connection subjected to a greater compression than the side of the bone which faces the setting element. When the load force has ceased, a tensile force acts in the opposite manner, owing to the elastic resetting tendency of the force support device. When there is an alternating normal force load, for example during walking, a tensile and thrust load occurs approximately axially in the fracture aperture. The rigidity of the force support device and the short bone screws bring about a sufficient degree of setting in all other directions of movement, so that no transverse forces or flexural and torsinal moments occur in the fracture gap.

The constriction of the connecting section in the direction of the wide side enables the device to be mounted so as to protect the tissues, with as little space as possible for the setting element in the area of the fracture zone, in order not to cause any additional circulatory disturbances.

The setting element may consist of two setting element parts which lie flat on top of each other, are fastened to each other in the end sections, and of which the connection sections can be moved away from each other by a spreader device. The spreader device may consist of a headless screw screwed into a threaded bore in the connection section of the one setting device part. In this arrangement the two setting element parts may be of differing thicknesses in the direction of their narrow ends, at least on their connection sections.

In this arrangement the force support device that forms the setting element is divided in the direction of its narrow side, for example into setting element parts, one thicker and one thinner, which lie flat on top of each other and which are rigidly connected to each other only in the area of the end sections, for example by means of screwing. In the area of the connection section, the two setting element parts can be spread from each other by means of a spreader device.

If in this case the thinner setting element part is positioned near to the bone, compression on the fracture fissure can be exerted by spreading in the area of the connection section. If, conversely, the thicker setting element part is positioned near to the bone, then the two fracture ends are moved away from each other by spreading in the area of the connection section which may be necessary for maintaining distance if the bone is fragmented. In both cases the resilient parts of the connection sections are retained whereas in the case of the force support carrier divided into two only the flexion characteristics have altered.

If the bone screws are seated in the end sections of the setting device in such a way that they can rotate, this will make a better adaptation to the individual fracture situation and correction of erroneous borings possible. Further, the bone screws can be mounted under pretension, which can, under certain circumstances, prevent a loosening tendency.

On the end sections of the setting element, guide sections for the shafts of the bone screws may be provided. The bone screws are secured against axial displacement in the setting elements by a tension device and are stabilised by a guide section, formed as a tapered segment, until immediately before they enter the bone.

The setting device according to the invention is used as follows:

Following the repositioning of the fracture, the force support device, formed by the setting element, is connected to the two bone ends, in that, firstly the anchoring holes are drilled in the bone corticalis with the aid of a boring stencil which has been screwed onto the force support device and, if necessary, an appropriate thread is subsequently cut. The bone screw is then grasped at its rear end with a tension tongue and rotated by the force support device into the bone until it finds a firm hold in the two opposite corticalis layers. This procedure is repeated for all the remaining fastening points of the force support device. The bone screws are now shortened at the height of the external surface of the force support device with a bolt clipper. The screws are axially fastened by means of a longitudinally slit cone which is pushed over the bone screw and, pressed by a screw which is provided with a flat head and holds the cut-off end of the bone screw in the centre, finds a secure hold in a counter support, which is also conical, in the area of the taper segment shaped guide.

If the force support device is in a divided form, then, when the setting device has been mounted, with the aid of the spreader device which is formed by the Imbus headless screw, the stress on the fracture zone can be applied or released. By means of a small incision in the skin, the headless screw can also be reached in the later stages of the fracture healing process, in order to adapt the elasticity of the force support device to the requirements of the particular stages in the healing of the fracture.

BRIEF DESCRIPTION OF THE DRAWINGS

With reference to the drawings embodiments of the invention will be explained in more detail. In the drawings:

FIG. 1 shows in perspective, a setting device, mounted over the fracture in a tubular bone;

FIG. 2 shows the setting device of FIG. 1, rotated through approxiamately 90°;

FIG. 6 shows in a view as for FIG. 1, a modification of the setting device;

FIG. 7 shows in cross section, the connection section shown as a detail A of FIG. 6 in the state where it has not been spread; and FIG. 8 shows in a view as for FIG. 7, the connection section in the spread state.

DESCRIPTION OF PREFERRED EMBODIMENTS

Figure 3:
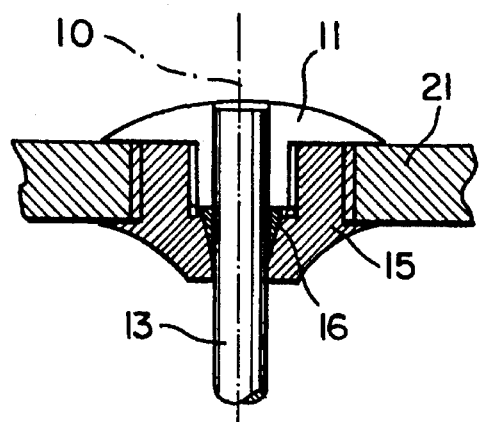
FIG. 3 shows in cross-section, the positive-locking securing of the bone screw in the setting element.

The tubular bone section 1 shown in FIGS. 1 and 2 is fractured along a first fracture line 4, which branches into two fracture lines 3, thereby forming a broken out segment 2, which is inserted again into the tubular bone section 1, the entire fracture being set with the aid of a setting element 20.

The setting element 20 has two end sections 2, which are connected to each other by a connection section 31. In each end section 21 two borings are provided, at a distance from each other, through which bone screws 40 are guided. Each bone screw 10 has a shaft 13 and a thread 14. The shaft 13 of each bone screw is guided in a taper segment shaped guide section 15, which is mounted on the setting element 20 on the side opposite the tubular bone section 1. The proximal end of the bone screw is surrounded by a screw 11 which is provided with a flat head and a central boring and comprises two diametrically positioned borings 12 for the engagement of the ends of a screwdriver of appropriate form.

The setting element 20 has a longitudinally extended flattened form with an essentially rectangular cross-section. The end sections 21 are relatively rigid. The cross-section thereof has two opposite wide sides 22 and two opposite narrow sides 23. The connection section 31 is resilient in comparison with the rigidity of the end sections 21, this being achieved in that the wide side 32 thereof is smaller than the wide side 22 of the end section 21 and in that the narrow side 33 thereof has a shorter extension than the arrow side 23 of the end section 21. In the embodiment shown in FIGS. 1 and 2 both the wide side 32 and the narrow side 33 of the connection section 31 are reduced in their extension with respect to the wide side 22 and the narrow side 23 of each end section 21, namely by approx. 40%.

As shown in FIG. 3, the bone screws 10 sit in the end section 21 in such a way that the shaft 13 thereof extends through a taper segment shaped guide section 15, the axial setting being achieved with the aid of a longitudinally slit cone 16 which is pressed into a counter-bearing in the taper segment shaped guide section 15 by the screw 11. The guide section 15 lies with its base over a large area on the end section 21 and is connected thereto in a force-locking manner.

Figure 4:
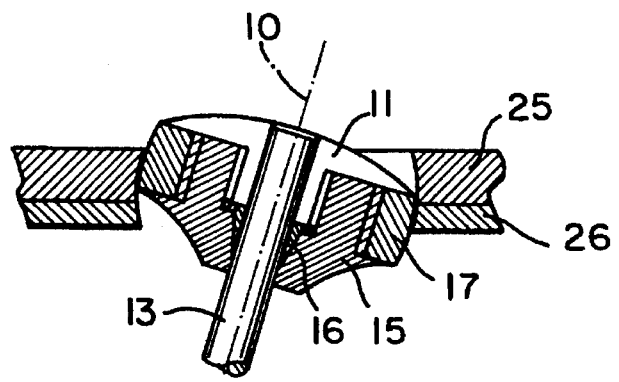
FIG. 4 shows in cross-section, the rotatable securing of the bone screw in the setting element rotated through approx. 20°.
Figure 5:
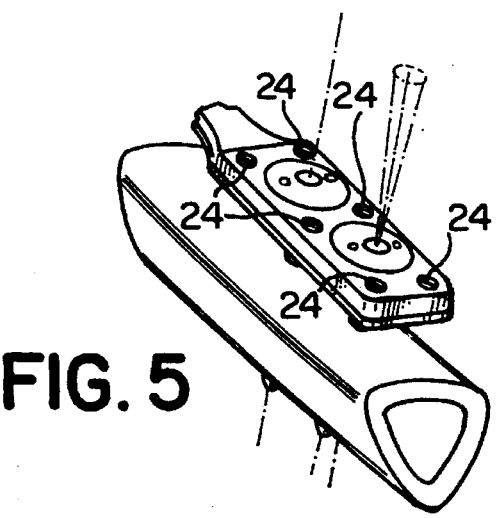
FIG. 5 shows in perspective, an end section of a setting device with a tubular bone to clarify the possibilities of rotation.

In the case of the modification shown in FIG. 4, the bone screw 11 is held by its shaft 13, together with the guide section 15 with the cone 16, in a spherical section 17 which is positioned in a rotatable manner in the setting element 20, which, in this embodiment, is formed by two setting element parts 25 end 26. By means of the force-locking setting of the spherical section 17 between the setting element parts 25 and 26, which are attached to each other by screws 24, as is shown in FIG. 5, the bone screw 10 can be rotated by a given amount and thus be screwed into a preliminary bore in the tubular bone section even if this preliminary bore is not exactly parallel to the preliminary bore for the other bone screw in the same end section.

In the case of the modification shown in FIGS. 6 to 8 the tubular bone section 1 has a continuous fracture aperture 4. The setting element 20 forming the force support carrier is divided, in the extension of its narrow side into two setting element parts 25 and 26 which lie flat one on top of the other so that the seperating seem also extends through the connection section 31, which is thus separated into a connection section 35, which is shown as being thick in FIGS. 6 to 8, and a connection section 36, which is shown as being thinner. The two setting element parts 25 and 26 are, in the area of their end sections 21, each fastened onto each other by four screws 24. In the thicker connection section 35, which faces away from the tubular bone section 1, an Imbus headless screw 34 is screwed into a threaded bore. With the aid of this Imbus headless screw 34, the connection section 36 facing the tubular bone section 1 can be moved from the position abutting in a flat manner shown in FIG. 7 to the outwardly curved position shown in FIG. 8, whereby the forces exerted on the tubular bone section 1 on both sides of the fracture aperture 4 can be altered.

I claim:

1. Setting device for tubular bone fractures, said device comprising:

A) a longitudinally extended flattened setting element comprised of tissue-compatible, high-density material, said setting element having:
   1) a cross-section which is essentially rectangular;
   2) rigid end sections, each having at least two bores extending through opposite wide sides thereof for guiding bone screws having a shaft through said end sections; and,
   3) a connection section extending between said rigid end sections, said connection section having a cross-section smaller than the cross-section of the end sections, B) means for positioning said setting element on the said bone screws in a spaced, non-contacting relationship with the surface of the tubular bone in the vicinity of the tubular bone fracture, and for providing a space between said setting device and the surface of the tubular bone in the vicinity of the tubular bone fracture; and C) means in and cooperating with the means for positioning and in the bores of the end sections of the setting element for axially securing the bone screws in the setting element and stabilizing the bone screws until immediately before the screws enter the bone.

2. Setting device according to claim 1, wherein each securing and stabilizing means comprises:

a longitudinally slit cone which can be pushed over the shaft of the bone screw and housed within a guide section in the means for positioning, said guide section provided with a conical counter-bearing; and, a flat-head screw with a bore for pressing the longitudinally slit cone into the conical counter-bearing.

3. Setting device according to claim 2, wherein the guide section lies with its base over a large area on the end section and is connected thereto in force-locking manner.

4. Setting device according to claim 2, wherein the guide section is held in a spherical section which is positioned in a rotatable and force-locking manner in a bore in the end section.

5. Setting device according to claim 1, wherein the cross-sectional area of the connection section, which is bordered by two narrow sides and two wide sides of the connection section (31), is reduced relative to the end sections (21) by reducing at least one of the dimensions (33) of the wide sides and the dimensions (32, 33) of the narrow and the wide sides of the connection section.

6. Setting device according to claim 5, wherein the dimensions (33) of the narrow sides of the connection section (31) are reduced by 30% to 70%.

7. Setting device according to claim 5, wherein the dimensions (32) of the wide sides of the connection section (31) are reduced by 30% to 70%.

8. Setting device according to claim 1, wherein the setting element (20) consists of two setting element parts (25, 26) which lie flat on top of each other and are connected to each other (24) in the end sections (21).

9. Setting device according to claim 8, wherein said overlapping connection sections (35, 36) of the setting device parts (25, 26) can be moved away from each other by a spreading device (34, 37).

10. Setting device according to claim 9, wherein the spreading device is a headless screw (34) screwed into a threaded bore (37) in the connection section (35) of the one setting element part (25).

11. Setting device according to claim 9, wherein the two setting element parts (25,26) are of differing thickness, at least in the connection section with respect to a narrow side of the element.

12. Setting device according to claim 8, wherein the two setting element parts (25,26) are of differing thickness, at least in the connection section with respect to a narrow side of the element.

* * * * *